US008728064B2

(12) United States Patent
Schomacker et al.

(10) Patent No.: US 8,728,064 B2
(45) Date of Patent: May 20, 2014

(54) DEVICES FOR THE TREATMENT OF BIOLOGICAL TISSUE

(75) Inventors: Kevin T. Schomacker, Maynard, MA (US); Xiaoming Shang, Lexington, MA (US); Hebert R. Otterson, Needham, MA (US); Antonio Paulino, Watertown, MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 13/316,775

(22) Filed: Dec. 12, 2011

(65) Prior Publication Data

US 2013/0150841 A1 Jun. 13, 2013

(51) Int. Cl.
*A61B 18/20* (2006.01)

(52) U.S. Cl.
USPC ............................................. 606/13

(58) Field of Classification Search
None
See application file for complete search history.

(56) References Cited

U.S. PATENT DOCUMENTS

| | | | | |
|---|---|---|---|---|
| 6,295,307 B1* | 9/2001 | Hoden et al. | | 372/36 |
| 6,413,252 B1* | 7/2002 | Zavislan | | 606/22 |
| 6,770,069 B1 | 8/2004 | Hobart et al. | | |
| 6,918,905 B2* | 7/2005 | Neuberger | | 606/9 |
| 2003/0004499 A1* | 1/2003 | McDaniel | | 606/3 |
| 2003/0216795 A1 | 11/2003 | Harth et al. | | |
| 2004/0156412 A1* | 8/2004 | Sun et al. | | 372/50 |
| 2006/0005484 A1* | 1/2006 | Riblier et al. | | 52/204.5 |
| 2006/0259102 A1* | 11/2006 | Slatkine | | 607/88 |
| 2006/0293727 A1 | 12/2006 | Spooner et al. | | |
| 2011/0226308 A1* | 9/2011 | Pang | | 136/246 |

FOREIGN PATENT DOCUMENTS

| | | |
|---|---|---|
| EP | 1074275 | 2/2001 |
| WO | 03/001984 | 1/2003 |
| WO | 2004000150 | 12/2003 |
| WO | 2007038567 | 4/2007 |
| WO | 2007/106339 | 9/2007 |
| WO | 2007/106856 | 9/2007 |
| WO | 2010060097 | 5/2010 |

OTHER PUBLICATIONS

Mert Serkan, Laser Beam Shaping Optical System Design Methods and Their Application in Edge-Emitting Semiconductor Laser-Based Lidar Systems, Ph.D. Dissertation, Auburn University, Dec. 17, 2007 (available at: http://etd.auburn.edu/etd/bitstream/handle/10415/159/Serkan_Mert_22.pdf?sequence=1).*
Osram, Product Datasheet for SPL BX81-2S, Apr. 20, 2007.*
International Search Report for PCT/US2012/067743 dated Mar. 22, 2013 (6 pages).
International Search Report and Written Opinion of the International Searching Authority for International Application No. PCT/US2012/067743, Date of Mailing Sep. 4, 2013, 19 pages.

* cited by examiner

*Primary Examiner* — Gary Jackson
*Assistant Examiner* — Scott T Luan
(74) *Attorney, Agent, or Firm* — Manelli Selter PLLC; Edward J. Stemberger (57) ABSTRACT

An apparatus for treating a subcutaneous fat region is provided. The apparatus includes a housing that has a skin contacting portion defining a chamber. The apparatus also includes a first spaced region in the housing through which a coolant passes and a second spaced region in the housing that is at least partially evacuated of air. The apparatus further includes a source of electromagnetic radiation, a source of vacuum in fluid communication with the chamber, and a source for the coolant.

19 Claims, 8 Drawing Sheets

DEVICES FOR THE TREATMENT OF BIOLOGICAL TISSUE

FIELD OF THE INVENTION

The invention relates generally to devices for treating biological tissue, and more particularly, to treatment devices with integrated electromagnetic radiation, cooling and vacuum functions.

BACKGROUND OF THE INVENTION

Lasers, lamps, and other sources of electromagnetic radiation are utilized for various dermatological treatments including, for example, treatment of subcutaneous fat, treatment of sweat glands and removal of unwanted hair. For many of these applications, electromagnetic radiation is to be delivered at a selected depth in biological tissue.

However, when treating a large area of tissue simultaneously using electromagnetic radiation, it becomes difficult to provide substantially uniform radiation over the entire area so that sufficient radiation is applied to all portions of the area to achieve the desired treatment, while no portion of the area has so much radiation exposure as to experience thermal damage. Therefore, energy-emitting devices are needed to permit optimized utilization and delivery of electromagnetic radiation to a target treatment area.

SUMMARY OF THE INVENTION

The invention, in various embodiments, provides energy-emitting devices for treating biological tissue. The devices provide optimized delivery of electromagnetic radiation to simultaneously treat a relatively large area of the biological tissue. The devices also offer integrated heat management capabilities, providing cooling for both the energy-emitting source and surface cooling of the biological tissue being irradiated. Furthermore, the devices can provide vacuum capabilities, which are utilized for pain reduction as well as to increase efficacy and safety of light-based dermatological treatments.

In one aspect, an apparatus for treating a subcutaneous fat region is provided. The apparatus includes a housing that has a skin contacting portion defining a chamber, which is defined by a bottom surface of a first transparent optic recessed in the chamber and a rim extending from the perimeter of the first transparent optic toward the skin contacting portion. The apparatus also includes a second transparent optic that includes a bottom surface spaced from a top surface of the first transparent optic. The second transparent optic is disposed in the housing. The first transparent optic and the second transparent optic define a first spaced region through which a coolant passes. The apparatus also includes a third transparent optic that includes a bottom surface spaced from a top surface of the second transparent optic. The third transparent optic is disposed in the housing. The second transparent optic and the third transparent optic define a second spaced region at least partially evacuated of air. The apparatus further includes a source of electromagnetic radiation disposed in the housing relative to a top surface of the third transparent optic. In addition, the apparatus includes a source of vacuum in fluid communication with the chamber. The source of vacuum is capable of removing air from inside the chamber so that a surface of skin overlying the subcutaneous fat region is drawn into contact with the bottom surface of the first transparent optic. The apparatus further includes a source for the coolant. The coolant flows through the first spaced region so that thermal energy is removed through the first transparent optic from an epidermal region and at least a portion of a dermal region overlying the subcutaneous fat region.

In another aspect, an apparatus for treating a subcutaneous fat region is provided. The apparatus includes a plurality of diode lasers spaced in a plurality of rows and columns and disposed in a housing to provide delivery of a substantially even distribution of electromagnetic radiation to a surface of skin overlying the subcutaneous fat region. The apparatus also includes a cooling device disposed in the housing relative to a bottom surface of the plurality of diode lasers for modulating a temperature of the surface of skin. The cooling device includes a first, second and third transparent optics through which the electromagnetic radiation is delivered to the surface of skin. The apparatus additionally includes a cooling manifold disposed in the housing relative to a top surface of the plurality of diode lasers. The cooling manifold is adapted to conduct liquid therethrough to cool the plurality of diode lasers. The apparatus further includes a distance gauge disposed in the housing between the plurality of laser diodes and the surface of skin. A height of the distance gauge, a distance between successive rows of the diodes, a distance between successive columns of the diodes or a combination thereof is adjustable to provide the substantially even distribution of the electromagnetic radiation.

In another aspect, an apparatus for treating a subcutaneous fat region is provided. The apparatus includes a source of vacuum in fluid communication with a chamber in a housing. The chamber is defined by a bottom surface of a cooling device recessed in the chamber and a rim extending from the perimeter of the bottom surface toward a skin contacting portion. The apparatus also includes a source of electromagnetic radiation disposed in the housing relative to a top surface of the cooling device for delivering, during at least a portion of a treatment period, an even distribution of the electromagnetic radiation simultaneously to a surface of skin overlying the subcutaneous fat region. The surface of skin has an area of at least 10 $cm^2$. In addition, the vacuum is adapted to remove air from inside the chamber during at least a portion of the treatment period so that the surface of skin is uniformly drawn into contact with the bottom surface of the cooling device without causing petechiae to the surface of skin.

In another aspect, an apparatus is provided for modulating a temperature of skin tissue overlying a subcutaneous fat region while treating the subcutaneous fat region using a source of electromagnetic radiation. The apparatus includes a first transparent optic disposed in a housing. The first transparent optic is adjacent to a skin contacting portion of the housing. The apparatus also includes a second transparent optic disposed in the housing. The second transparent optic includes a bottom surface spaced from a top surface of the first transparent optic. The first transparent optic and the second transparent optic define a first spaced region through which a coolant passes to remove thermal energy from an epidermal region of the skin tissue, a dermal region of the skin tissue, or the subcutaneous fat region or a combination thereof. The apparatus additionally includes a third transparent optic disposed in the housing. The third transparent optic includes a bottom surface spaced from a top surface of the second transparent optic. The second transparent optic and the third transparent optic define a second spaced region at least partially evacuated of air.

In some embodiments, the apparatus further includes a chamber in the housing defined by a bottom surface of the first transparent optic recessed in the chamber and a rim extending from the perimeter of the first transparent optic toward the skin contacting portion. In some embodiments, the source of electromagnetic radiation is disposed in the housing relative to a top surface of the third transparent optic. In some embodiments, the apparatus further includes a source of vacuum in fluid communication with the chamber. The source of vacuum is adapted to remove air from inside the chamber so that a surface of skin overlying the subcutaneous fat region is drawn in contact with the bottom surface of the first transparent optic.

In other examples, any of the aspects above can include one or more of the following features. At least one of the transparent optics can be sapphire. In some embodiments, the first transparent optic is sapphire. The second spaced region of the apparatus can house a thermally insulative gas. The skin contacting portion can flatten the surface of skin or compress the surface of skin, or a combination thereof, while the subcutaneous fat region is being treated.

In some embodiments, the apparatus further includes a controller in electrical communication with the source of electromagnetic radiation and the source of vacuum. The controller receives a signal when a threshold value of pressure is reached. The controller then triggers the source of electromagnetic radiation to deliver the electromagnetic radiation to the subcutaneous fat region.

In some embodiments, the source of electromagnetic radiation includes a plurality of diode lasers. The plurality of laser diodes can be spaced in a plurality of rows and columns to provide delivery of a substantially even distribution of the electromagnetic radiation to the surface of skin. Adjacent columns can be spaced by about 5 mm and adjacent rows can be spaced by about 20 mm. The plurality of laser diodes can include a diode laser bar having 10 diode lasers along each row and 5 diodes along each column. Each laser diode can have about a 12-degree divergence along a row direction, which is the axis perpendicular to the p-n junction of the laser diode, and about a 45-degree divergence along a column direction, which is the axis parallel to the p-n junction. In some embodiments, the power emitted by each laser diode is about 3 W. In some embodiments, the fluence rate of each laser diode is about 2 W/cm$^2$, after accounting for transmission losses through the optics and coolant fluid.

In some embodiments, the apparatus can supply a substantially same amount of current to each of the plurality of laser diodes. In some embodiments, the apparatus can supply different amounts of current to at least two of the plurality of laser diodes to compensate for variations in efficiency among the laser diodes.

In some embodiments, the apparatus can further include a distance gauge between the plurality of the laser diodes and the skin contacting portion. A height of the distance gauge, a distance between successive rows of the diodes, a distance between successive columns of the diodes, or a combination thereof can be adjusted to provide the substantially even distribution of the electromagnetic radiation.

The source of electromagnetic radiation can provide radiation having a wavelength of about 1,200 nm to about 1,230 nm and a power density of less than or equal to about 2.3 W/cm$^2$.

The apparatus can deliver the electromagnetic radiation simultaneously to the surface of skin having an area of at least 50 cm$^2$. The apparatus can deliver the electromagnetic radiation for at least 300 seconds.

The apparatus can further include a cooling manifold in communication with the source of electromagnetic radiation. The cooling manifold is configured to conduct liquid therethrough to cool the source of electromagnetic radiation. In some embodiments, the coolant in the first spaced region additionally removes thermal energy from at least a portion of the subcutaneous fat region, such as the upper subcutaneous fat region, and from the skin overlaying the portion of subcutaneous fat region.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

Figure 1:
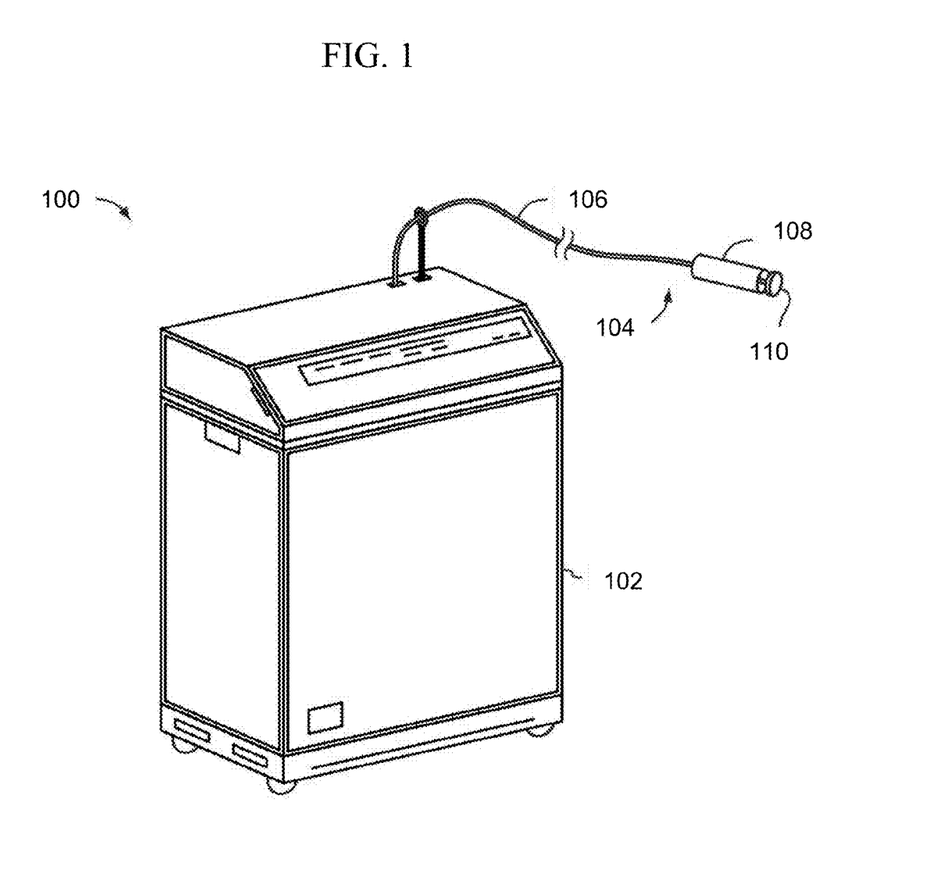
FIG. 1 shows an embodiment of a system for treating biological tissue.

FIG. 1 shows an embodiment of a system 100 for treating biological tissue. The system 100 can be used to non-invasively deliver radiation to a target region. For example, the radiation can be delivered through an external surface of skin over the target region. The system 100 includes an energy source 102 and a delivery system 104. In one embodiment, radiation provided by the energy source 102 is directed via the delivery system 104 to a target region. In the illustrated embodiment, the delivery system 104 includes an umbilical cable 106 having a circular cross-section and an applicator 108. The umbilical cable 108 can house at least one of an electrical power line, a vacuum line and a coolant line connected to the applicator 108. The applicator 108 can include laser diodes and/or an optical system (e.g., an optic or system of optics) to direct the radiation to the target region. The applicator 108 can be a handheld device, such as a handpiece, which can be held or manipulated by a user to irradiate the target region. The delivery system 104 can be positioned in contact with a skin surface, adjacent a skin surface, proximate a skin surface, spaced from a skin surface, or a combination thereof. In the embodiment shown, the delivery system 104 includes a spacer 110 to space the delivery system 104 from the skin surface. A spacer 110 is not required however. In one embodiment, the spacer 110 can be a distance gauge, which can aid a practitioner with placement of the delivery system 104.

To minimize unwanted thermal injury to tissue not targeted (e.g., an exposed surface of the target region and/or the epidermal layer), the delivery system 104 can include a cooling system (not shown) for cooling before, during or after delivery of radiation, or a combination thereof. Cooling can include contact conduction cooling, evaporative spray cooling (using a solid, liquid, or gas), convective air flow cooling, or a combination thereof. If cooling is used, it can cool the most superficial layers of tissue overlying the intended treatment area. Cooling can facilitate leaving the overlying skin intact during laser treatment.

Figure 2:
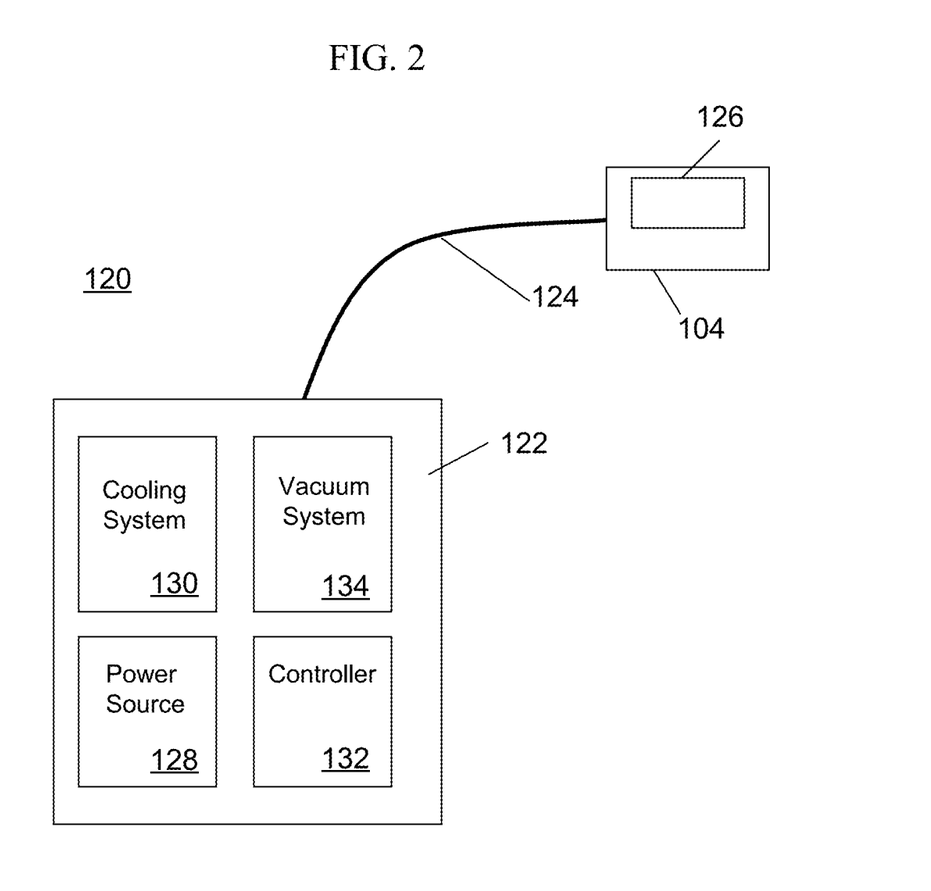
FIG. 2 shows another embodiment of a system for treating biological tissue.

FIG. 2 shows another embodiment of a system 120 for treating biological tissue. The system 120 is configured to form a pattern of treatment zones in skin. System 120 can include a base unit 122 coupled to an umbilicus 124, which is connected to a delivery module 104. The base unit 122 includes a power source 128 that supplies power to various system components, including an energy source 126 housed in the delivery module 104. The base unit 122 also includes a controller 132, which can be coupled to a user interface and can include a processing unit. The base unit 122 can include a cooling system 130 for cooling the skin surface and the delivery module 104, such as cooling one or more laser diodes of the delivery module 104. The base unit 122 can also include a vacuum system 134.

The system 120 can be used to non-invasively deliver an array of radiation beams to a target region of the skin. For example, the array of radiation beams can be delivered through an external surface of skin over the target region. In one embodiment, a beam of radiation provided by the energy source 126 is directed via the delivery module 104 to a target region. The umbilicus 124 can act as a conduit for communicating power, signal, vacuum, fluid and/or gas between the base unit 122 and the delivery module 104. The umbilicus 124 can include a fiber to deliver radiation from the base unit 122 to the delivery module 104. The delivery module 104 can include an optical system (e.g., an optic or a system of optics) to convert a beam of radiation into an array of radiation beams and direct the array to the target region. The delivery module 104 can supply electrical power from power source 128 to the energy source 126. The delivery module 104 can include one or more laser diodes or light-emitting diodes, or include one or more optical fibers delivering light from a source such as laser diodes. The optical system can include a mask or focusing system to provide radiation having regions where no treatment radiation is delivered (e.g., to create a pattern of undamaged tissue or skin surrounded by damaged tissue or skin). A user can hold or manipulate the delivery module 104 to irradiate the target region. The delivery module 104 can be positioned in contact with a skin surface, adjacent a skin surface, proximate a skin surface, spaced from a skin surface, or a combination thereof. In some embodiments, an array of radiation beams can be formed from a single beam of radiation by a system of optics.

To minimize unwanted thermal injury to tissue not targeted (e.g., an exposed surface of the target region and/or the epidermal layer), the delivery module 104 can include a cooling module for cooling before, during or after delivery of radiation, or a combination thereof. Cooling can include contact conduction cooling, evaporative spray cooling, convective air flow cooling, or a combination of the aforementioned.

In various embodiments, the energy source 102 of the system 100 or the energy source 126 of the system 120 can be an incoherent light source or a coherent light source (e.g., a laser). The energy sources 102, 126 can be broadband or monochromatic. The radiation can be a pulsed beam, a scanned beam, or a gated continuous wave (CW) beam. The laser can be a diode laser, a solid state laser, a fiber laser, or the like. An incoherent source can be a light emitting diode (LED), a flashlamp (e.g., an argon or xenon lamp), an incandescent lamp (e.g., a halogen lamp), a fluorescent light source, or an intense pulsed light system. The incoherent source can include appropriate filters to block unwanted electromagnetic radiation. The energy sources 102, 126 can be housed in the system console or in an applicator, such as a handpiece.

Figure 3:
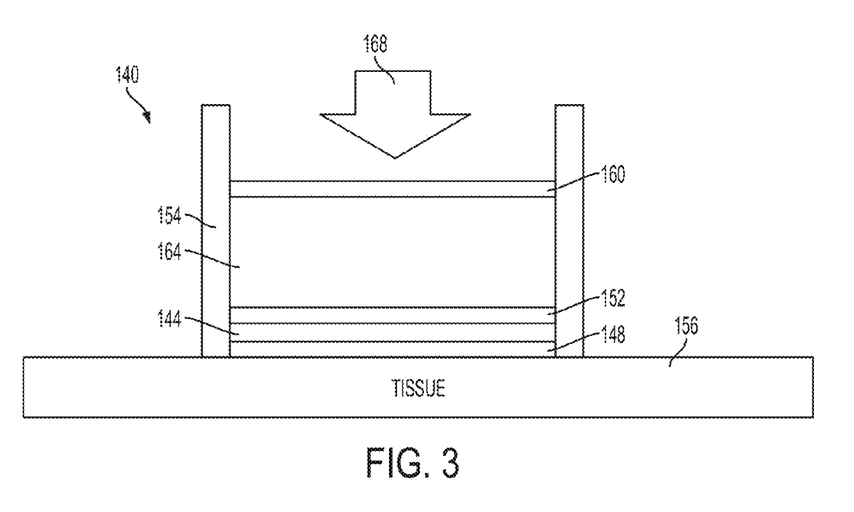
FIG. 3 shows an exemplary cooling portion of an applicator.

FIG. 3 shows an exemplary cooling portion 140 of an applicator, which can be the applicator 108 of the system 100 or the delivery module 104 of the system 120. The cooling portion 140 can include a coolant chamber 144 formed by two optical windows 148, 152 and sidewalls 154. Cooled refrigerant is passed through the flow chamber 144, cooling the window 148 that is in contact with a surface of skin 156, thereby cooling the skin surface 156.

One disadvantage of a one-chamber design is that it also cools the exterior of the window 152, which can lead to water droplets or frost forming on the exterior of the window 152 due to condensation of atmospheric water vapor. Condensation is generated depending on the temperature of the refrigerant and relative humidity. To avoid condensation, the cooling portion 140 includes a third optical window 160 to form a second chamber 164 defined by the windows 152, 160 and the sidewalls 154. The second chamber 164 can be filled with either a thermally insulating gas, such as argon, krypton, or dry nitrogen. In some embodiments, the second chamber 164 is fully or partially evacuated.

The first optical window 148 can be made from a substance that has good thermal conductivity such as crystalline sapphire. Each of the windows 148, 152 and 160 can be a sapphire or glass window. In an exemplary configure, the first optical window 148 is made of sapphire while the second window 152 and the third window 160 are made of glass or other material(s) of low thermal conductivity to minimize condensation. All of the windows 148, 152 and 160 as well as the chilled coolant fluid in the coolant chamber 144 can be transparent to the intended wavelength(s) of the applied laser radiation 168.

In some embodiments, the coolant chamber 144 can allow a flow of chilled coolant. The coolant can be chilled water, a fluorocarbon type cooling fluid such as chilled Fluorinert, a cryogenic fluid, or the like. The coolant can be transparent to the radiation 168 used during treatment. The coolant chamber 144 can allow sufficient flow of the coolant to avoid a significant increase in the water temperature in the chamber 144. The coolant chamber 144 can include one or more plenums or ports to avoid eddies within the chamber 144. For some laser wavelengths where the coolant can absorb the laser radiation, the coolant chamber 144 can be made sufficiently thin to avoid excessive absorption of the laser energy by the fluid in the chamber 144. Minimizing the thickness of the coolant chamber 144 can also facilitate an even flow of the coolant through the chamber 144 and decreases the required cross-sectional area of the coolant supply line and coolant return line. In some example, the coolant chamber 144 is about 0.5 mm thick.

The second chamber 164 can be purged, filled with argon, and sealed. Alternatively, the second chamber 164 can be evacuated and filled with krypton or some other thermally insulating gas.

The upper and lower surfaces of the third optical window 160 can be coated with an antireflective film chosen to minimize reflection at the laser wavelength(s). The upper surface of the second optical window 152, which is the surface facing the second chamber 164, can be coated with an antireflective film chosen to minimize reflection at the laser wavelength(s).

Figure 4:
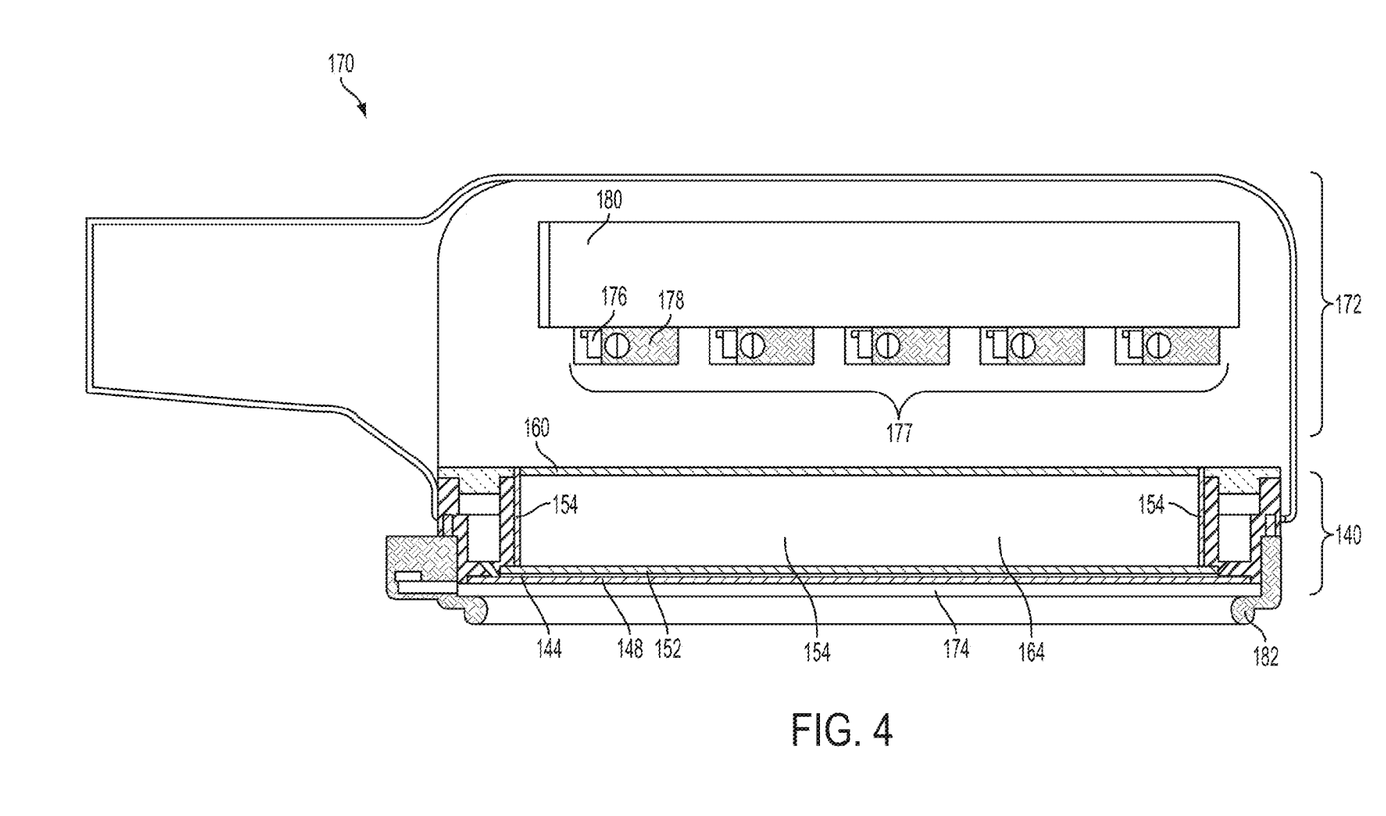
FIG. 4 shows a side view of an exemplary applicator.

FIG. 4 shows a side view of an exemplary applicator 170, which can be the applicator 108 of the system 100 or the delivery module 104 of the system 120. The applicator 170 can incorporate the cooling portion 140 as described above with reference to FIG. 3, a source of electromagnetic radiation 172 and a vacuum chamber 174.

The cooling portion 140 includes the first, second and third optical windows 148, 152, 160. The cooling portion 140 also includes the coolant chamber 144, defined by the windows 148, 152 and the sidewalls (not shown), to allow a flow of chilled coolant through the chamber 144. The cooling portion 140 further includes the second chamber 164 that is fully or partially evacuated and filled with an insulating gas, such as argon. Surfaces defining the second chamber 164 include the sidewalls 154, the lower surface of the third window 160 facing the second chamber 164 and the upper surface of the second window 152 facing the second chamber 164. In some embodiments, the upper and lower surfaces of the third window 160 and the upper surface of the second window 152 are coated with an antireflective film to minimize reflection of the laser generated by the electromagnetic radiation source 172. In some embodiments, the inner surfaces of the sidewalls 154 facing the second chamber 164 are coated with a reflective film to maximize reflection of the laser generated by the electromagnetic radiation source 172 and smooth the laser distribution at the edge of the treatment area. In some embodiments, a bottom surface of the first optical window 148 is adapted to contact a skin surface during treatment and is thus suitably configured to flatten and/or compress the skin surface.

The vacuum chamber 174 of the applicator 170 is defined by the bottom surface of the first optical window 148 that is recessed in the chamber 174 and a rim 182 extending from the perimeter of the bottom surface of the first optical window 148 to make contact with the skin. Specifically, the vacuum chamber 174 is exposed to a surface of skin overlying a target treatment region such that when air is removed from inside the chamber 174, the skin surface is drawn into contact with the bottom surface of the first optical window 148. In some embodiments, a source of vacuum (not shown) is in fluid communication with the vacuum chamber 174 to remove air from the chamber 174. In some embodiments, the rim 182 includes a skin-contacting portion that, when placed on the skin surface, spatially confines the treatment area to the enclosed tissue.

In various embodiments, vacuum applied to the vacuum chamber 174 ensures that the skin surface through which the treatment beam passes is in good contact with the cooling window 148 during surface cooling, which establishes a safer treatment environment and facilitates pain reduction. In addition, vacuum in the vacuum chamber 182 can hold the applicator 170 in place, thereby providing hand-free treatment. This is particularly useful when treatment times are long.

In various embodiments, the electromagnetic radiation source 172 includes a plurality of lasers 176 for generating sufficient electromagnetic radiation to be delivered to a target tissue region through the cooling portion 140, the vacuum chamber 174 and the skin surface overlying the target region. The lasers 176 can be diode lasers or other light-emitting lasers. If the lasers 176 are diode lasers, they can be made of indium phosphide (InP), indium gallium arsenide phosphide (InGaAsP), or another suitable material.

The lasers 176 can form a laser array 177 with one or more rows and columns to deliver a substantially even distribution of the electromagnetic radiation to the skin overlying the targeted region. In some embodiments, one or more cooling bars 178 are provided to cool at least one surface of each of the lasers 176. In addition, the electromagnetic radiation source 172 includes one or more cooling manifolds 180 in thermal communication with the laser array 177 to provide additional cooling.

Figure 5:
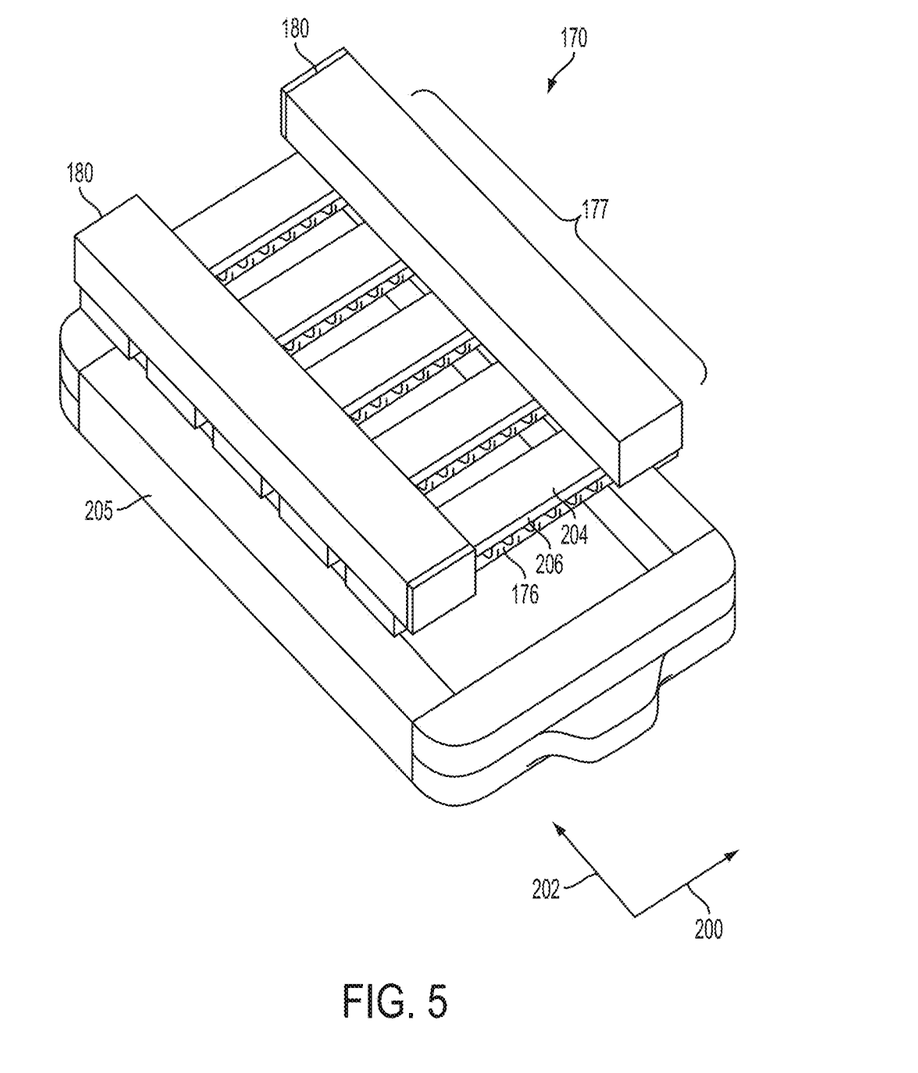
FIG. 5 shows a top view of an exemplary applicator.

FIG. 5 shows a top view of the exemplary applicator 170 of FIG. 4. For the purpose of illustration, the lasers 176 of the electromagnetic source 172 are arranged in an array 177 of five rows along the y-axis 202, with each row having ten lasers spaced along the x-axis 200. Each row of ten lasers 176 can be attached to a laser bar 204 along one or both sides of the bar 204 and aligned with the x-axis 200. In addition, the output emission of the lasers 176 is directed to the lower surface of the laser bar 204, which is the surface facing the skin when the applicator 170 is operated during treatment. As shown, the laser array 177 includes five laser bars 204 uniformly spaced along the y-axis 202. In other embodiments, however, there can be more than or fewer than five laser bars 204 included in the electromagnetic source 172. There can be more than or fewer than ten lasers 176 attached to each of the laser bars 204. The number of laser bars 204 and/or the number of lasers 176 per bar can be selected based on the size and shape of the treatment region.

In some embodiments, each laser 176 is mounted on the lower surface of the respective laser bars 204 using one or more 5 mm×5 mm ceramic mounts 206, which can have high thermal conductivity and low electrical conductivity. For example, a single, appropriately-sized ceramic mount 206 can be used to hold lasers 176 to an entire laser bar 204, such as ten lasers 176 per laser bar 204. In some embodiments, one or more 3 mm×5 mm ceramic mounts 206 are used to attach more lasers 176 to each laser bar 204. In some embodiments, each ceramic mount 206 is about 1 mm or less in thickness. Thinner mounts 206 can optimize heat conduction from the lasers 176 to the treatment area. The ceramic mounts 206 can be fabricated from materials with high thermal conductivity, such as aluminum nitride or beryllium oxide. In some embodiments, a ceramic mount 206 has a thermal conductivity greater than about 150 W/m-K and a dielectric constant greater than about 5.

In some embodiments, a cooling channel (not shown) is disposed within each laser bar 204. The cooling channel can substantially span the length of a laser bar 204 to provide uniform cooling to the lasers 176 coupled to each bar 204. Two cooling manifolds 180 can be coupled to the upper surface of the laser bars 204. Each cooling manifold 180 can simultaneously overlap all the laser bars 204 to provide a uniform flow of coolant to the cooling channels in the laser bars 204, thereby uniformly cools the lasers 176. The coolant can be water maintained between about 5 C and about 25 C or between 20 C to about 25 C. In some embodiments, the coolant flowing through the cooling channels and the cooling manifolds 180 is from the same source as the coolant provided to the coolant chamber 144 of the cooling portion 140. In some embodiments, even though the same coolant is provided to the coolant chamber 144, the cooling channel, and the cooling manifolds 180, the coolant flowing through each of the three components is maintained at a different temperature. In some embodiments, different coolants are provided to the three components.

As shown in FIG. 5, the applicator 170 can also include a distance gauge 205 to maintain a distance between the laser array 177 and the skin surface. In some embodiments, the distance gauge is about 36.7 mm high, capable of maintaining a distance of about 36.7 mm between the laser array 177 and the skin surface.

Figure 6:
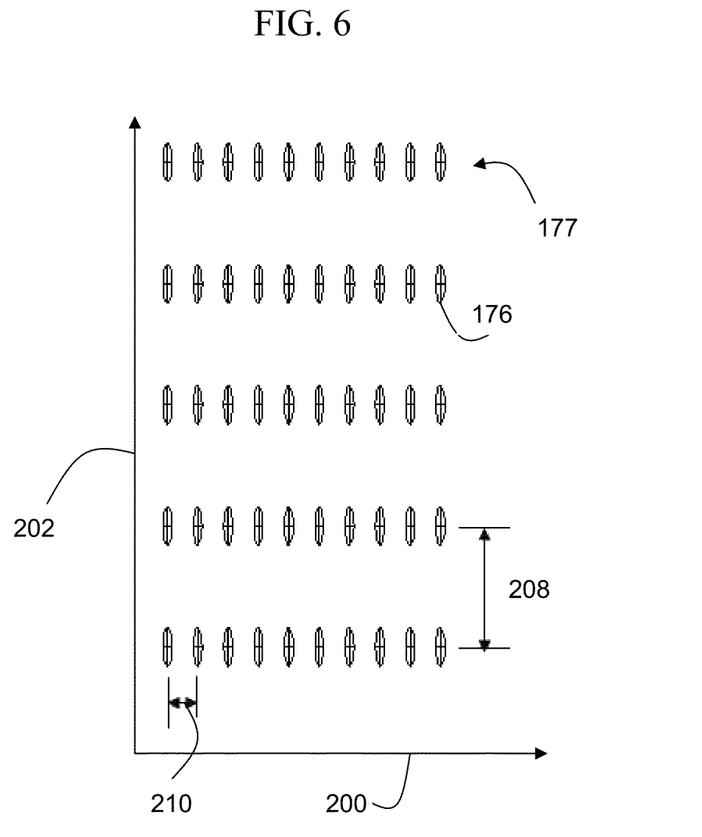
FIG. 6 shows an exemplary laser array of an applicator.

FIG. 6 shows an exemplary laser array 177 of the applicator 170. A y-distance 208 of about 20 mm can be maintained between two successive rows of the lasers 176 in the array 177 and a x-distance 210 of about 5 mm can be maintained between two successive columns of the lasers 176. This arrangement 177 can deliver a substantially uniform distribution of electromagnetic radiation to a surface area of about 10 cm along the y-axis 202 and about 5 cm along the x-axis 200. In some embodiments, every other row in the array 177 is offset from the adjacent rows by half of the x-distance 210 along the x-axis 200, such as by about 2.5 mm if the y-distance is about 5 mm.

Each laser 176 can have an elliptical electromagnetic radiation distribution pattern that is mathematically approximated by a two-dimensional Gaussian distribution having a fast axis, which represents the axis perpendicular to the p-n junction of the laser, and a slow axis, which represents the axis parallel to the p-n junction of the laser. In some embodiments, the lasers 176 are arranged such that their fast axis corresponds to the y-axis 202. The angle of divergence (FWHM) for the fast axis of each laser 176 can be greater than 30 degrees, such as approximately 37 degrees or 45 degrees. Therefore, if the distance gauge 205 of the applicator 170 is 36.7 mm in height (i.e., the distance between the lasers 176 and the skin surface is about 36.7 mm), the FWHM beam diameter of each laser 176 along the y-axis 202 is approximately 30.4 mm. In some embodiments, the lasers 176 are arranged such that their slow axis corresponds to the x-axis 200. The angle of divergence (FWHM) for the slow axis of each laser 176 can be approximately 12 degrees. Therefore, if the distance gauge 205 is about 36.7 mm in height, the FWHM beam diameter of each laser 176 along the x-axis 200 is approximately 7.71 mm. However, because the electromagnetic radiation generated by the laser array 177 is delivered to the skin surface through the first, second and third optical windows 148, 152, 160 of the cooling portion 140 as well as through the coolant in the coolant chamber 144 and/or the gas in the second chamber 164 of the cooling portion 140, the actual x-axis and y-axis diameters of the lasers 176 in the laser array 177 may be slightly different than the given approximations.

In general, any one of the x-distance 210, the y-distance 208, and the vertical distance between the lasers 176 and the skin surface, which can be represented by the height of the distance gauge 205, can be adjusted to achieve a relatively even energy distribution over the treatment area, even though each individual laser 176 may have a Gaussian-like beam. In some embodiments, because the x-distance 210 and the y-distance 208 are dependent on the distance between the lasers 176 and the skin surface, by fixing one of the three values, the other two values can be determined to achieve a relatively uniform energy distribution over a treatment area. As an example, the x-distance 210 (denoted as $g_x$) is first set to a fixed value, such as about 5 mm, which is about the same as the thickness of the ceramic mount 206 so that the lasers 176 are about 5 mm apart along the x-axis 200. In addition, the slow-axis divergence (denoted as $ang_s$) is a constant value, such as about 12 degrees. Then, the distance between the lasers 176 and the skin surface (denoted as $d_z$) can be suitably optimized using Equation 1 below to achieve an overall uniform beam distribution along the x-axis 200:

$$d_z = \frac{g_x}{2 \times \tan\left(\frac{ang_s}{2}\right)} \times \{\text{Overlap Factor}\} \quad \text{(Equation 1)}$$

The overlap factor of Equation 1 can be a value selected between 1 and 10, where 1 minimizes the number of lasers used to cover a fixed area. However, the fewer the number of lasers used, the more susceptible beam uniformity is to diode energy variations, including to dropped (e.g., burned-out) diodes. In contrast, a larger overlap factor corresponds to the use of more diodes to illuminate the same fixed area. However, the resulting beam uniformity is less sensitive to energy variations and dropped diodes. In addition, because the height of the applicator 170 is larger than and dependent on the distance $d_z$ between the lasers 176 and the skin surface, the height of the applicator 170 can be reduced by reducing the distance $g_x$ between the diodes placed along the x-axis 200, as shown in Equation 1. Equation 1 also shows that the value of the overlap factor affects the height of the applicator 170 as well.

After optimizing the distance $d_z$ between the lasers 176 and the skin surface, the placement of diodes along the y-axis 202, as represented by the y-distance 208 (denoted as $g_y$), can be optimized to achieve an overall uniform beam distribution along the y-axis 202. Specifically, using $d_z$ computed from Equation 1 and the fast-axis divergence value (denoted as $ang_f$), which can be about 45 degrees, the distance $g_y$ can be suitably optimized using Equation 2 below:

$$g_y = 2d_z \times \tan\left(\frac{ang_f}{2}\right) / \{\text{Overlap Factor}\} \quad \text{(Equation 2)}$$

The overlap factor of Equation 2 can be selected to be the same as or different from the overlap factor of Equation 1.

In various embodiments, the number of lasers 176 used, including the number of lasers 176 per row and/or the number of lasers per column of the laser array 177, is determined based on the size and/or shape of the treatment area. For example, the laser array 177, which includes 50 lasers organized in a 5-row-by-10-column formation, can treat a rectangular area of 10 cm (along the y-axis 202) by 5 cm (along the x-axis 200) if the y-distance 208 is set to about 20 mm between successive rows and the x-distance 210 is set to about 5 mm between successive columns. In some examples, the treatment area can be circular or elliptically, having a diameter between about 1 cm and about 6 cm. In some examples, the surface of skin can have an area of at least 10 cm² or at least 50 cm².

In various embodiments, the laser array 177 is configured to produce an electromagnetic radiation wavelength of between about 400 nm to about 4000 nm, although longer and shorter wavelengths can be produced depending on the application. In certain embodiments, the wavelength of the electromagnetic radiation is fat selective. For example, the ratio of coefficients of absorption of fat to water is about 0.5 or greater. The wavelength can be about 875 nm to about 950 nm or about 1175 nm to about 1250 nm. For example, the wavelength can be about 900 nm to about 940 nm or about 1200 nm to about 1240 nm. The wavelength can be about 1200 nm to about 1230 nm. In some embodiments, the wavelength is about 1210 nm. In some embodiments, multiple laser arrays can be used to achieve a desired wavelength. For example, a first laser array producing electromagnetic radiation of about 1210 nm can be combined with a second laser array producing electromagnetic radiation from about 400 nm to about 10.6 microns, the combination of which can be further coupled to an RF source, or with an ultrasonic source.

In some examples, the wavelength is non-fat selective, e.g., about 950 nm to about 1090 nm, about 1100 nm to about 1160 nm, about 1,300 nm to about 1625 nm or about 1,800 nm to about 2,200 nm.

In some examples, the wavelength is selected to penetrate a surface of skin and reach the underlying subcutaneous fat region so as to cause damage to the fat cells in the subcutaneous fat region.

In various embodiments, the power and/or power density of the electromagnetic radiation generated by the laser array 177 is adjustable by changing the current supplied to the individual lasers 176. For the laser array 177 shown in FIG. 6, if each laser 177 emits a power of about 2 W, such as about 2.4 W, the total power for the entire 50-laser array 177 is about 120 W. Because the area covered by the array 177 is about 50 cm$^2$ (5 cm×10 cm) if the x-distance 210 is about 5 mm and the y-distance 208 is about 20 mm, the average power density provided by the laser array 177 is about 2 W/cm$^2$ after accounting for transmission losses through the cooling chamber. In general, the laser power delivered to a treatment area can be about 25 W to about 125 W, although higher or lower power can be generated depending on the application. In some embodiments, the laser power can be about 90 W to about 110 W. In some embodiments, power density of about 0.5 W/cm$^2$ to about 2.5 W/cm$^2$ is delivered to the skin surface.

Figure 7A:
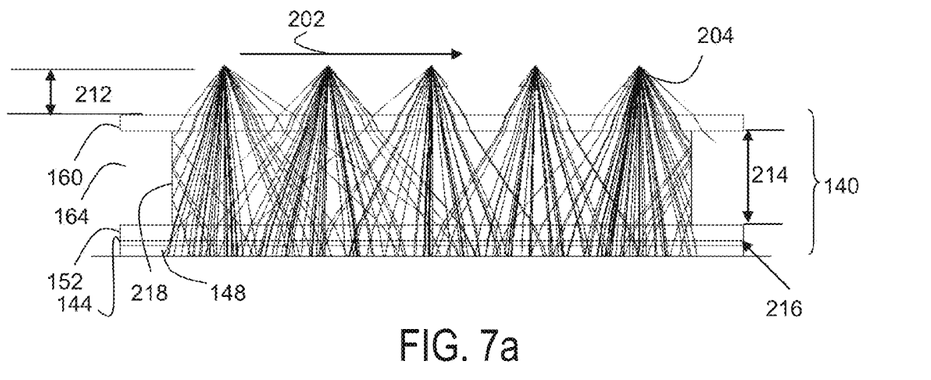
FIGS. 7a and 7b show various views of an exemplary laser power density distribution pattern produced using an applicator.

FIG. 7a shows a profile view of an exemplary laser power density distribution pattern produced using the laser array 177 of the applicator 170. Specifically, to produce the distribution pattern shown in FIG. 7a, the laser array 177 includes five laser bars 204 spaced along the y-axis 202 with each bar 204 including ten lasers 176 spaced along the x-axis 200. The y-distance 208 between successive rows of the lasers 176 is about 20 mm and the x-distance 210 between successive columns of the lasers 176 is about 5 mm.

The laser array 177 is arranged on top of the cooling portion 140 of the applicator 170 such that a vertical distance 212 between the top of the laser array 177 and the upper surface of the third optical window 160 of the cooling portion 140 is about 10 mm. The third optical window 160 can be about 3 mm thick. The second chamber 164 of the cooling portion 140, which is bounded above and below by the third optical window 160 and the second optical window 152, respectively, can be about 18.2 mm in thickness 214. The second optical window 152 can be about 3 mm thick. The cooling portion 140 also includes the coolant chamber 144 that is bounded above and below by the second optical window 152 and the first optical window 148, respective. The thickness 216 of the coolant chamber 144 can be about 0.5 mm. The first optical window 148 can be about 2 mm thick. Overall, a distance of about 36.7 mm can be maintained between the top of the laser bars 204 and the bottom surface of the first optical window 148. In some embodiments, a distance gauge (not shown) can be used to maintain this distance. In some embodiments, one or more mirrors 218 or other reflective surfaces can be suitably positioned along the boundary of a treatment area to define the treatment area and reflect the laser beams so as to smooth the laser distribution at the boundary.

Figure 7B:
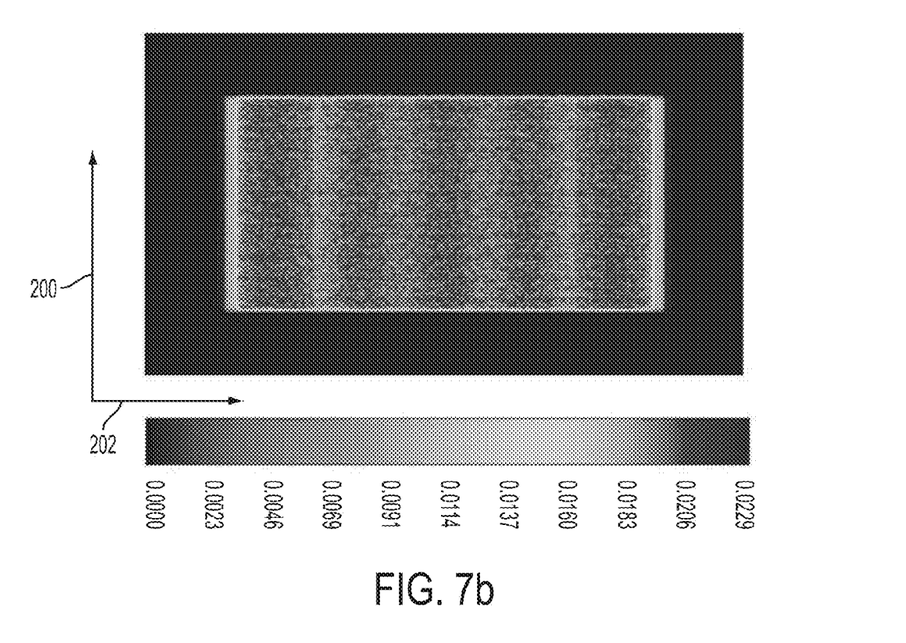

FIG. 7b shows a top view of a laser power density distribution pattern measured at the skin surface when operating the applicator 170. The treatment surface is about 10 cm along the y-axis 202 and 5 cm along the x-axis 200. The distribution pattern shows a relatively homogenous power density distribution with a peak irradiance of about 0.0229 W/cm$^2$. In addition, the total power measured at the skin surface is about 0.99 W.

Figure 8A:
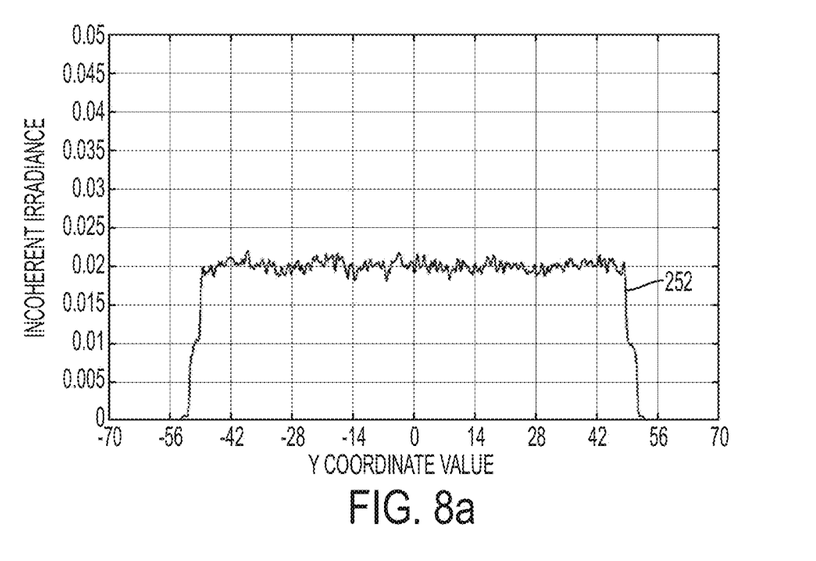
FIGS. 8a and 8b show exemplary laser power density distribution measured at a skin surface along the x-axis and the y-axis, respectively.
Figure 8B:
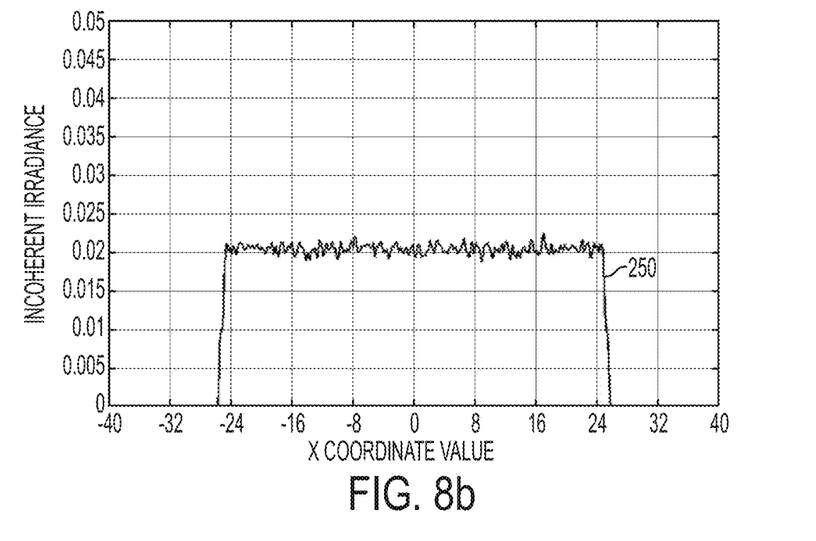

FIGS. 8a and 8b show the laser power density distribution measured at the skin surface along the y-axis 202 and the x-axis 200, respectively. As shown in FIG. 8a, the power density distribution 252 extends nearly uniformly along a length of the treatment area (about 10 cm), which is parallel to the y-axis 202. Specifically, the power density distribution 252 only fluctuates slightly around 0.02 W/cm$^2$. Similarly, as shown in FIG. 8b, the power density distribution 250 extends nearly uniformly along a width of the treatment area (about 5 cm), which is parallel to the x-axis 200. As shown, the power density distribution 250 only fluctuates slightly around 0.02 W/cm$^2$.

In some examples, substantially the same amount of current is supplied to each of the laser 176 in the laser array 177. In some examples, the current supplied to one or more of the lasers 176 vary to compensate for variation in the efficiency among the lasers 176. Due to the partial overlap of Gaussian beams produced by the individual lasers 176, up to about 20% variations in power among the lasers 176 may be acceptable, provided that the lasers 176 are randomly distributed and not clustered together based on power, such that lower (or higher) powered lasers are adjacent to each other.

In various embodiments, the radiation can have exposure duration between about 3 s and about 1800 s, although longer and shorter exposure durations can be used depending on the application. In some embodiments, the radiation can have exposure duration of at least 300 seconds, such as about 300 seconds to about 600 seconds. In some embodiments, a longer exposure time permits radiation to treat at a greater depth into the subcutaneous fat region in comparison to radiation having a shorter exposure time, providing that all other parameters are the same. In certain examples, if the power intensity of the applied radiation is sharply increased and then lowered during several time intervals, the treatment duration is less than 300 seconds, such as about 140 seconds to about 300 seconds. The treatment time can be even shorter if the power intensity is increased slightly after the lowering period.

In various embodiments, power density and treatment duration can be selected to treat a subcutaneous fat region of a subject. For example, an average power density of the electromagnetic radiation generated by the array 177 of the applicator 170 is between about 0.5 W/cm$^2$ to about 5 W/cm$^2$ and the electromagnetic radiation can be delivered to the skin surface to treat the subcutaneous fat region for about 40 seconds or longer, such as about 40 seconds to about 600 seconds. In some embodiments, the average power density is less than or equal to about 2 W/cm$^2$, such as about 0.5 W/cm$^2$ to about 2 W/cm$^2$. In some embodiments, the radiation is delivered to the subcutaneous fat region for at least about 300 seconds, such as about 300 seconds to about 600 seconds. The peak power density of the applied radiation can exceed 2 W/cm$^2$, as long as the average power density over a treatment period is less than or equal to about 2 W/cm$^2$. In some embodiments, the average power density of the electromagnetic radiation delivered is less than or equal to about 2.3 W/cm$^2$. In some embodiments, multiple pulses of radiation can be delivered to the subcutaneous fat region and the sum of the pulse durations reaches the desired treatment duration.

In some examples, to treat the subcutaneous fat region, the region can be heated to a temperature of between about 47° C. and about 80° C., although higher and lower temperatures can be used depending on the application. In one embodiment, the temperature is between about 50° C. and about 55° C. In one embodiment, the temperature is about 50° C.

In various embodiments, the radiation delivered to the treatment area using the applicator 170 can have a fluence of about 50 J/cm$^2$ to about 1500 J/cm$^2$, although larger or smaller fluence can be used depending on the application.

In various embodiments, the parameters of the radiation can be selected to deliver the electromagnetic radiation to a predetermined depth. In some embodiments, the radiation can be delivered to the target region about 0.005 mm to about 10 mm below an exposed surface of the skin, although shallower or deeper depths can be selected depending on the application. In some embodiments, the depth is about 1 mm to about 3.5 mm. In some embodiments, the depth is greater than or equal to 3 mm below the surface of skin, where the subcutaneous fat region resides.

In various embodiments, an optical system is used to deliver radiation to a large area beam or as a pattern of beamlets (e.g., a plurality of microbeams having a spotsize of about 0.1-5 mm) to form a pattern of thermal injury within the biological tissue.

In various embodiments, one or more sensors can be positioned relative to a target region of skin. For example, a sensor can be positioned in contact with, spaced from, proximate to, or adjacent to the skin target. A sensor can determine a temperature on a surface of the target region, in the target region, or remote from the target region. One or more sensors can also be positioned at various locations in the applicator 170 to monitor for example, the temperature of the coolant flowing through the coolant chamber 144, the amount of vacuum applied in the vacuum chamber 174, and/or the average laser power in the laser portion 174 of the applicator 170. The sensor can be a thermistor, an array of thermistors, a thermopile, a thermocouple, a thermometer, a resistance thermometer, and a thermal-imaging based sensor, a thermographic camera, an infrared camera or any combination thereof.

In various embodiments, the applicator 170 can include rollers to massage the skin. For example, skin in the target region or adjacent to the target region can be massaged and/or vibrated before, during, and/or after irradiation of the target region of skin. The massage can be a mechanical massage or can be manual massage. In one embodiment, the applicator 170 can provide an additional massage effect by using vacuum, such as the vacuum generated by the vacuum chamber 174, to pull the tissue into the device 170. Massaging the target region of skin can facilitate removal of the treated fatty tissue from the target region. For example, massaging can facilitate draining of the treated fatty tissue from the treated region. Vibrating and/or massaging the skin in the target region or adjacent to the target region during irradiation can also reduce or alleviate treatment pain and allow treatment using higher power densities.

In various embodiments, a controller is used to automate the treatment process. The controller is in electrical communication with the laser portion 172, the cooling portion 174 and/or the vacuum chamber 174 of the applicator 170. For example, the controller can automatically initiate a radiation exposure sequence after detecting that the skin has established full contact with the first optical window 148 of the applicator 170, or after detecting that sufficient vacuum is applied to the skin if vacuum is used in the vacuum chamber 174 to draw the skin into contact with the first optical window 148. The controller can dynamically select the power density and exposure duration for delivering electromagnetic radiation to a treatment area, such as to a subcutaneous fat region. If different power densities are used for different time intervals during treatment, the controller can also automatically determine the optimal power density and exposure time for each of the time intervals.

In addition, the power density and exposure duration can be determined by the controller based on the thickness of the skin. For example, the intensity of light reaching the subcutaneous layer decreases with increasing overlying skin thickness due to increase light scattering and absorption in skin, so increased power is required to cause sufficient thermal damage in the subcutaneous fat. Therefore, the thickness of the skin can be measured over the area of the body to be treated such that the treatment fluence and exposure time can be selected and controlled for each individual and the body area to be treated. In some embodiments, skin thickness can be measured using ultrasonography at about 10 to 20 MHz for example.

In operation, the laser sequence generated by the laser array 177 of the applicator 170 can be triggered by pressing a switch on the applicator 170, stepping on a food pedal, or automatically triggered after sensing a sufficient differential vacuum in the vacuum chamber 174, such as when the vacuum level exceeds 5 in Hg. An exemplary laser sequence includes a pre-cool period, followed by a laser-on period and followed by a post-cool period. In certain embodiments, the pre-cool and the post-cool periods are not necessary if the average laser power density is about 2 W/cm$^2$.

In various embodiments, the applicator 170 can apply the electromagnetic radiation to the skin in a stamping mode or by scanning a light source along a surface of the skin. A computerized pattern generator can be used with the applicator 170 or the applicator 170 can be manually manipulated to scan the light source.

Processors suitable for the execution of computer programs for operating the applicator 170 include, by way of example, both general and special purpose microprocessors, and any one or more processors of any kind of digital computer. A processor can receive instructions and data from a read-only memory or a random access memory or both. A processor also includes, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The treatment radiation generated by the applicator 170 can damage one or more fat cells so that at least a portion of lipid contained within can escape or be drained from the treated region. At least a portion of the lipid can be carried away from the tissue through biological processes. In one embodiment, the body's lymphatic system can drain the treated fatty tissue from the treated region. In an embodiment where a fat cell is damaged, the fat cell can be viable after treatment. In one embodiment, the treatment radiation can destroy one or more fat cells. In one embodiment, a first portion of the fat cells is damaged and a second portion is destroyed. In one embodiment, a portion of the fat cells can be removed to selectively change the shape of the body region.

In some embodiments, the treatment radiation can be delivered to the target region to thermally injure, damage, and/or destroy one or more fat cells. For example, the radiation can be delivered to a target chromophore in the target region. Suitable target chromophores include, but are not limited to, a fat cell, lipid contained within a fat cell, fatty tissue, a wall of a fat cell, water in a fat cell, and water in tissue surrounding a fat cell. The energy absorbed by the chromophore can be transferred to the fat cell to damage or destroy the fat cell. For example, thermal energy absorbed by dermal tissue can be transferred to the fatty tissue. In one embodiment, the radiation is delivered to water within or in the vicinity of a fat cell in the target region to thermally injure the fat cell.

In various embodiments, treatment radiation can affect one or more fat cells and can cause sufficient thermal injury in the dermal region of the skin to elicit a healing response to cause the skin to remodel itself. This can result in more youthful looking skin and an improvement in the appearance of cellulite. In one embodiment, sufficient thermal injury induces fibrosis of the dermal layer, fibrosis on a subcutaneous fat region, or fibrosis in or proximate to the dermal interface. In one embodiment, the treatment radiation can partially denature collagen fibers in the target region. Partially denaturing collagen in the dermis can induce and/or accelerate collagen synthesis by fibroblasts. For example, causing selective thermal injury to the dermis can activate fibroblasts, which can deposit increased amounts of extracellular matrix constituents (e.g., collagen and glycosaminoglycans) that can, at least partially, rejuvenate the skin. The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, and/or reduce discoloration of the skin.

In various embodiments, the treatment radiation can cause a zone of thermal injury formed at or proximate to the dermal interface. Fatty tissue has a specific heat that is lower than that of surrounding tissue (fatty tissue, so as the target region of skin is irradiated, the temperature of the fatty tissue exceeds the temperature of overlying and/or surrounding dermal or epidermal tissue. For example, the fatty tissue has a volumetric specific heat of about 1.8 $J/cm^3$ K, whereas skin has a volumetric specific heat of about 4.3 $J/cm^3$ K. In one embodiment, the peak temperature of the tissue can be caused to form at or proximate to the dermal subcutaneous fat interface. For example, a predetermined wavelength, fluence, pulse duration, and cooling parameters can be selected to position the peak of the zone of thermal injury at or proximate to the dermal subcutaneous fat interface. This can result in collagen being formed at the bottom of the dermis and/or fibrosis at or proximate to the dermal interface. As a result, the dermal interface can be strengthened against fat herniation. For example, strengthening the dermis can result in long-term improvement of the appearance of the skin since new fat being formed or untreated fat proximate the dermal interface can be prevented and/or precluded from crossing the dermal interface into the dermis. Targeted heating at the dermal subcutaneous fat interface can also affect the base of eccrine and/or apocrine glands to reduce sweating, thus helpful to subjects with hyperhidrosis or bromhidrosis.

In one embodiment, fatty tissue is heated by absorption of radiation, and heat can be conducted into dermal tissue proximate the fatty tissue. The fatty tissue can be disposed in the dermal tissue and/or can be disposed proximate to the dermal interface. A portion of the dermal tissue (e.g., collagen) can be partially denatured or can suffer another form of thermal injury, and the dermal tissue can be thickened and/or be strengthened as a result of the resulting healing process. In such an embodiment, a fat-selective wavelength of radiation can be used.

In one embodiment, water in the dermal tissue is heated by absorption of radiation. The dermal tissue can have disposed therein fatty tissue and/or can be overlying fatty tissue. A portion of the dermal tissue (e.g., collagen) can be partially denatured or can suffer another form of thermal injury, and the dermal tissue can be thickened and/or be strengthened as a result of the resulting healing process. A portion of the heat can be transferred to the fatty tissue, which can be affected. In one embodiment, water in the fatty tissue absorbs radiation directly and the tissue is affected by heat. In such embodiments, a water selective wavelength of radiation can be used.

In various embodiments, a treatment can cause minimal cosmetic disturbance so that a subject can return to normal activity following a treatment. For example, a treatment can be performed without causing discernible side effects such as bruising, open wounds, burning, scarring, or swelling. Furthermore, because side effects are minimal, a subject can return to normal activity immediately after a treatment or within a matter of hours, if so desired.

In various embodiments, an ultrasound device can be used to measure the depth or position of the fatty tissue. For example, a high frequency ultrasound device operating at 10 MHz to 20 MHz can be used. An applicator of an ultrasound device can be placed proximate to the skin to make a measurement. In one embodiment, the ultrasound device can be placed in contact with the skin surface. The ultrasound device can deliver ultrasonic energy to measure position of the dermal interface, so that radiation can be directed to the interface.

The time duration of the cooling and of the radiation application can be adjusted so as to maximize the thermal injury to the vicinity of the dermal interface and avoid injury to overlying epidermal and dermal tissue. For example, if the position of the fatty tissue is known, then parameters of the optical radiation, such as pulse duration and/or fluence, can be optimized for a particular treatment. Cooling parameters, such as cooling time and/or delay between a cooling and irradiation, can also be optimized for a particular treatment. Accordingly, a zone of thermal treatment can be predetermined and/or controlled based on parameters selected. For example, the zone of thermal injury can be positioned in or proximate to the dermal interface.

While the invention has been particularly shown and described with reference to specific illustrative embodiments, it should be understood that various changes in form and detail may be made without departing from the spirit and scope of the invention.

The invention claimed is:

1. A handheld apparatus for treating a subcutaneous fat region, comprising:

a housing including a skin contacting portion defining a chamber, wherein the chamber is defined by a bottom surface of a first transparent optic recessed in the chamber and a rim extending from the perimeter of the first transparent optic toward the skin contacting portion of the housing, wherein the chamber is exposed to a surface of skin overlying the subcutaneous fat region;

a second transparent optic including a bottom surface spaced from a top surface of the first transparent optic, the second transparent optic disposed in the housing, the first transparent optic and the second transparent optic defining a first spaced region through which a coolant passes without being directly exposed to the surface of skin;

a third transparent optic including a bottom surface spaced from a top surface of the second transparent optic, the third transparent optic disposed in the housing, the second transparent optic and the third transparent optic defining a second spaced region filled with a thermally insulating gas, thereby at least preventing or reducing condensation on the second transparent optic caused by the coolant passing through the first spaced region;

a source of electromagnetic radiation disposed in the housing relative to a top surface of the third transparent optic, wherein the source of electromagnetic radiation comprises a plurality of diode lasers integrated in the housing;

a source of vacuum in fluid communication with the chamber, the source of vacuum capable of removing air from inside the chamber so that the surface of skin overlying the subcutaneous fat region is drawn into contact with the bottom surface of the first transparent optic; and a source for the coolant, the source flowing the coolant through the first spaced region so that thermal energy is removed through the first transparent optic from an epidermal region and at least a portion of a dermal region overlying the subcutaneous fat region.

2. The apparatus of claim 1 wherein at least the first transparent optic comprises sapphire.

3. The apparatus of claim 1 wherein the thermally insulative gas comprises Krypton.

4. The apparatus of claim 1 further comprising a controller in electrical communication with the source of electromagnetic radiation and the source of vacuum, the controller receiving a signal when a threshold value of pressure is reached, the controller triggering the source of electromagnetic radiation to deliver the electromagnetic radiation to the subcutaneous fat region.

5. The apparatus of claim 4 wherein the controller is configured to trigger the source of electromagnetic radiation to deliver the electromagnetic radiation to the subcutaneous fat region for at least 300 seconds.

6. The apparatus of claim 5 wherein the source of electromagnetic radiation is adapted to provide radiation having a wavelength of 1,200 nm to 1,230 nm and a power density of less than or equal to 2.3 W/cm$^2$.

7. The apparatus of claim 6 wherein the controller is configured to deliver the electromagnetic radiation simultaneously to the surface of skin having an area of at least 50 cm$^2$.

8. The apparatus of claim 1 wherein the skin contacting portion is adapted to flatten the surface of skin, or compress the surface of skin, or a combination thereof, while the subcutaneous fat region is being treated.

9. The apparatus of claim 1 wherein the plurality of laser diodes are spaced in a plurality of rows and columns to provide delivery of an even distribution of the electromagnetic radiation to the surface of skin.

10. The apparatus of claim 9 wherein adjacent columns are spaced by 5 mm and adjacent rows are spaced by 20 mm.

11. The apparatus of claim 9 wherein the plurality of laser diodes are attached to a plurality of diode laser bars, wherein each diode laser bar includes one or more laser diodes spaced at a first regular interval and the plurality of diode laser bars are spaced at a second regular interval from each other.

12. The apparatus of claim 9 wherein each laser diode has a 12-degree divergence along a row direction and a 45-degree divergence along a column direction.

13. The apparatus of claim 9 further comprising a distance gauge between the plurality of the laser diodes and the skin contacting portion.

14. The apparatus of claim 13 wherein a height of the distance gauge, a distance between successive rows of the diodes, a distance between successive columns of the diodes, or a combination thereof is adjusted to provide the substantially even distribution of the electromagnetic radiation.

15. The apparatus of claim 9 wherein the power emitted by each laser diode is 2.5 W.

16. The apparatus of claim 9 further comprising supplying a same amount of current to each of the plurality of laser diodes.

17. The apparatus of claim 9 further comprising supplying different amounts of current to at least two of the plurality of laser diodes to compensate for variations in efficiency among the laser diodes.

18. The apparatus of claim 1 further comprising a cooling manifold in communication with the source of electromagnetic radiation, the cooling manifold is configured to conduct liquid therethrough to cool the source of electromagnetic radiation.

19. The apparatus of claim 1 wherein the coolant removes thermal energy from at least a portion of the subcutaneous fat region and overlying skin.

* * * * *